(12) United States Patent
Kaula et al.

(10) Patent No.: US 6,466,817 B1
(45) Date of Patent: Oct. 15, 2002

(54) NERVE PROXIMITY AND STATUS DETECTION SYSTEM AND METHOD

(75) Inventors: Norbert F. Kaula, Arvada, CO (US); Jeffrey J. Blewett, San Diego; James F. Marino, La Jolla, both of CA (US)

(73) Assignee: NuVasive, Inc., San Diego (*) Notice: Subject to any disclaimer, the term of this patent is extended or adjusted under 35 U.S.C. 154(b) by 0 days.

(21) Appl. No.: 09/590,632

(22) Filed: Jun. 8, 2000

Related U.S. Application Data
(60) Provisional application No. 60/167,416, filed on Nov. 24, 1999.

(51) Int. Cl.⁷ .............................. A61B 5/05; A61B 5/04
(52) U.S. Cl. ...................... 600/546; 600/554; 600/547; 607/118
(58) Field of Search .................. 600/546, 547, 600/548, 554; 607/72, 115, 116, 117, 118; 606/34, 41

(56) References Cited

U.S. PATENT DOCUMENTS

| | | | |
|---|---|---|---|
| 2,704,064 A | 3/1955 | Fizzell et al. | 600/554 |
| 3,364,929 A | 1/1968 | Ide et al. | 600/554 |

(List continued on next page.)

FOREIGN PATENT DOCUMENTS

| | | |
|---|---|---|
| WO | WO 00/66217 | 11/2000 |

OTHER PUBLICATIONS

Ford et al., "Electrical characteristics of peripheral nerve stimulators implications for nerve localization" *Regional Anesthesia* (1984) 9:73–77.

Greenblatt et al., "Needle nrve simulator–locator: Nerve blocks with a new instrument for locating nerves" *Anesthesia & Analgesia* (1962) 41(5):599–602.

Martin et al., "Initiation of erection and semen release by rectal probe electrostimulation (RPE)"*The Williams & Wilkins Co.* (1983) pp. 637–642.

Pither et al., "The use of peripheral nerve stimulators for regional anesthesia: Review of experimental characteristics, technique, and clinical applications" *Regional Anesthesia* (1985) 10:47–53.

Raj et al., "Infraclavicular brachial plexus block—A new approach" *Anesthesia and Analgesia* (1973) 52(6):897–904.

Raj et al., "Use of the nerve stimulator of peripheral blocks" *Regional Anesthesia* (Apr.–Jun. 1980) pp. 14–21.

Raj et al., "The Use of peripheral nerve stimulators for regional anesthesia" *Clinical Issues in Regional Anesthesia* (1985) 1(4):1–6.

Raymond et al., "The nerve seeker: A system for automated nerve localization" *Regional Anesthesia* (1992) 17(3):151–162.

Shafik, "Cavernous nerve stimulation through an extrapelvic subpubic approach: Role in penile erection" *Eur. Urol.* (1994) 26:98–102.

*Primary Examiner*—Kevin Shaver
*Assistant Examiner*—Charles Marmor, II
(74) *Attorney, Agent, or Firm*—Jonathan Spangler

(57) ABSTRACT

A method and system for detecting proximity of a nerve to a proximity electrode and status of nerve. The method of detecting the proximity of the nerve to the proximity electrode applies a first electrical signal with multiple current levels to a calibration electrode. The method applies a second electrical signal with multiple current levels to the proximity electrode. Based on the response of the nerve to the first and second electrical signals, the method determines the proximity of the proximity electrode to the nerve. The method determines the status of the nerve by applying the first electrical signal with multiple signal levels to the calibration electrode.

118 Claims, 7 Drawing Sheets

U.S. PATENT DOCUMENTS

| | | | | |
|---|---|---|---|---|
| 3,664,329 | A | 5/1972 | Naylor | 600/554 |
| 3,682,162 | A | 8/1972 | Colyer | 600/373 |
| 3,830,226 | A | 8/1974 | Staub et al. | 600/554 |
| 3,957,036 | A | 5/1976 | Normann | 600/377 |
| 4,099,519 | A | 7/1978 | Warren | 600/554 |
| 4,207,897 | A | 6/1980 | Lloyd et al. | 606/28 |
| 4,224,949 | A | 9/1980 | Scott et al. | 600/373 |
| 4,235,242 | A | 11/1980 | Howson et al. | 600/508 |
| 4,285,347 | A | 8/1981 | Hess | 607/117 |
| 4,515,168 | A | 5/1985 | Chester et al. | 600/554 |
| 4,519,403 | A | 5/1985 | Dickhudt | 607/117 |
| 4,545,374 | A | 10/1985 | Jacobson | 600/61 |
| 4,592,369 | A | 6/1986 | Davis et al. | 600/546 |
| 4,633,889 | A | 1/1987 | Talalla et al. | 607/117 |
| 4,658,835 | A | 4/1987 | Pohndorf | 607/118 |
| 4,759,377 | A | 7/1988 | Dykstra | 600/546 |
| 4,807,642 | A | 2/1989 | Brown | 600/546 |
| 4,892,105 | A | 1/1990 | Prass | 607/116 |
| 4,926,865 | A | 5/1990 | Oman | 607/59 |
| 4,962,766 | A | 10/1990 | Herzon | 600/554 |
| 4,964,411 | A | 10/1990 | Johnson et al. | 600/546 |
| 5,007,902 | A | 4/1991 | Witt | 604/117 |
| 5,058,602 | A | 10/1991 | Brody | 600/546 |
| 5,081,990 | A | 1/1992 | Deletis | 600/555 |
| 5,092,344 | A | 3/1992 | Lee | 600/554 |
| 5,127,403 | A | 7/1992 | Brownlee | 607/122 |
| 5,161,533 | A | 11/1992 | Prass et al. | 600/372 |
| RE34,390 | E | 9/1993 | Culver | 600/554 |
| 5,255,691 | A | 10/1993 | Otten | 607/117 |
| 5,282,468 | A | 2/1994 | Klepinski | 600/377 |
| 5,284,153 | A | 2/1994 | Raymond et al. | 600/554 |
| 5,284,154 | A | 2/1994 | Raymond et al. | 600/554 |
| 5,313,956 | A | * 5/1994 | Knutsson et al. | 600/554 |
| 5,375,067 | A | 12/1994 | Berchin | 702/66 |
| 5,482,038 | A | 1/1996 | Ruff | 600/372 |
| 5,540,235 | A | * 7/1996 | Wilson | 600/554 |
| 5,560,372 | A | 10/1996 | Cory | 600/554 |
| 5,566,678 | A | 10/1996 | Cadwell | 600/554 |
| 5,579,781 | A | 12/1996 | Cooke | 600/546 |
| 5,593,429 | A | 1/1997 | Ruff | 607/116 |
| 5,630,813 | A | 5/1997 | Kieturakis | 606/46 |
| 5,671,752 | A | 9/1997 | Sinderby et al. | 600/546 |
| 5,711,307 | A | 1/1998 | Smits | 600/546 |
| 5,775,331 | A | 7/1998 | Raymond et al. | 600/554 |
| 5,779,642 | A | 7/1998 | Nightengale | 600/461 |
| 5,797,854 | A | 8/1998 | Hedgecock | 600/554 |
| 5,830,151 | A | 11/1998 | Hadzic et al. | 600/554 |
| 5,851,191 | A | 12/1998 | Gozani | 600/554 |
| 5,853,373 | A | 12/1998 | Griffith et al. | 600/554 |
| 5,885,219 | A | 3/1999 | Nightengale | 600/461 |
| 5,888,196 | A | 3/1999 | Bonutti | 600/204 |
| 5,928,158 | A | 7/1999 | Aristides | 600/547 |
| 5,976,094 | A | * 11/1999 | Gozani | 600/483 |
| 6,004,262 | A | 12/1999 | Putz et al. | 600/114 |
| 6,038,477 | A | 3/2000 | Kayyali | 607/72 |
| 6,050,992 | A | 4/2000 | Nichols | 606/41 |
| 6,132,386 | A | 10/2000 | Gozani et al. | 600/554 |
| 6,132,387 | A | 10/2000 | Gozani et al. | 600/554 |
| 6,146,335 | A | 11/2000 | Gozani | 600/554 |
| 6,161,047 | A | 12/2000 | King et al. | 607/62 |
| 6,224,549 | B1 | 5/2001 | Drongelen | 600/300 |
| 6,259,945 | B1 | * 7/2001 | Epstein et al. | 600/547 |
| 6,266,558 | B1 | * 7/2001 | Gozani et al. | 600/547 |

* cited by examiner

NERVE PROXIMITY AND STATUS DETECTION SYSTEM AND METHOD

CROSS-REFERENCES TO RELATED APPLICATIONS

The present application is a regular patent application of and claims the benefit of priority from U.S. Provisional Patent Application Serial No. 60/167,416, filed Nov. 24, 1999, assigned to the Assignee hereof and is incorporated by reference herein.

BACKGROUND OF THE INVENTION

1. Field of the Invention

This invention relates to nerve monitoring systems and to nerve muscle monitoring systems, and more particularly to nerve proximity and status detection methods and systems.

2. Description of Related Art

Systems and methods exist for monitoring a nerve. One such system determines when a needle is approaching a nerve. The system applies a current to the needle to evoke a muscular response. The muscular response is visually monitored, (typically as a shake or "twitch"). When such a muscular response is observed by the user, the needle is considered to be near the nerve coupled to the responsive muscle. These systems require the user to observe the muscular response (to determine that the needle has approached the nerve). This may be difficult depending on the competing tasks of the user. In addition, when general anesthesia is used during a procedure, muscular response may be suppressed, limiting the ability of a user to detect the response.

Accordingly, a need exists for a better system and method that can determine the proximity of a needle, catheter, or other device to a nerve or group of nerves.

SUMMARY OF THE INVENTION

The present invention includes a method and system for determining the status of a nerve, in particular a nerve motor unit (where the nerve is connected to a set of muscle fibers which contracts). The present invention also includes a method and system for determining the proximity of a nerve (motor unit) to a conductive device. In order to determine the status of a nerve, the invention applies an electrical signal to a conductive device or element. The conductive element is positioned near the nerve. The electrical signal includes a number of current levels applied over time. Each of the current levels is applied to the conductive element and thus to the nerve. The response of the nerve to each current level is measured. The response of the nerve to the stimulus may be detected by an electromyogram ("EMG"). The EMG response of the nerve may be measured at a muscle that is physiologically coupled to the nerve (motor unit). In a preferred aspect, the present invention determines the status of the nerve based on the measured response of the nerve to the current levels applied thereto.

To determine the status of the nerve based on the response, the present invention may map the response of the nerve for each current level. The mapping is based on the level of each response at a fixed period of time or latency of the response. The present invention uses the mapping of the responses of the nerve to the current levels to determine the status of the nerve. This information may be used to determine the health of the nerve and may be gathered real time such as during a surgery or other medical procedure. In such a case, the conductive element may be coupled to a catheter, a needle, a cannula or another medical device. The fixed latency period used to map the responses may be determined as a function of peaks in each response. The maximum magnitude peak in each response is determined and then the latency period having the largest number of peaks located contemporaneously in the responses is selected as the fixed latency period to be used to map the responses. The sum of the ratio of peak level to current level for the maximum magnitude peak of each response may also be determined. The latency having the largest sum of ratios of peak level to current level is then selected as the fixed latency.

In order to determine the proximity of a nerve to a conductive element such as a proximity electrode, the present invention applies a first electrical signal to a calibration electrode. The calibration electrode includes a conductive element that is located or positioned near the nerve. The present invention then applies a second electrical signal to the proximity electrode. The first and second electrical signals include a number of current levels applied at different time intervals. Each of the current levels is applied to the proximity electrode and calibration electrode and thus to the nerve. The response of the nerve to each current level from each electrode is measured. For example, the response of the nerve to each stimulus may be detected by an electromyogram ("EMG"). The EMG response of the nerve may be measured at a muscle that is physiologically coupled the nerve. The present invention determines the relative proximity of the nerve to the proximity electrode by comparing the responses of the nerve to the first signal and to the second signal. Optionally, the present invention may also compare the slope (change in voltage/change to current (dV/dI)) of the responses of the nerve to the first signal and the second signal.

The present invention may also map the response of each current level of the first signal and map the response of each current level of the second signal. Then, the relative proximity of the nerve to the proximity electrode may be determined by comparing each mapping. The mapping of each signal is based on the level of response at a fixed period of time or latency of the response. The determined proximity may be used to guide a real time procedure such as during a surgery or other medical procedure. In such a case the proximity electrode may be coupled to a catheter, a needle, a cannula or another medical device. The fixed latency used to map the response of each signal may be determined as a function of peaks in each response. The maximum magnitude peak in each response is determined and then the latency having the largest number of maximum magnitude peaks located contemporaneously in each response is selected as the fixed latency. The sum of the ratio of peak level to current level for the maximum magnitude peak of each response may also be determined. The latency having the largest sum of ratios of peak level to current level is selected as the fixed latency accordingly.

BRIEF DESCRIPTION OF THE DRAWINGS

Like reference numbers and designations in the various drawings indicate like elements.

DESCRIPTION OF THE SPECIFIC EMBODIMENTS

Throughout this description, the preferred embodiment and examples shown should be considered as exemplars, rather than as limitations on the present invention.

Figure 1:
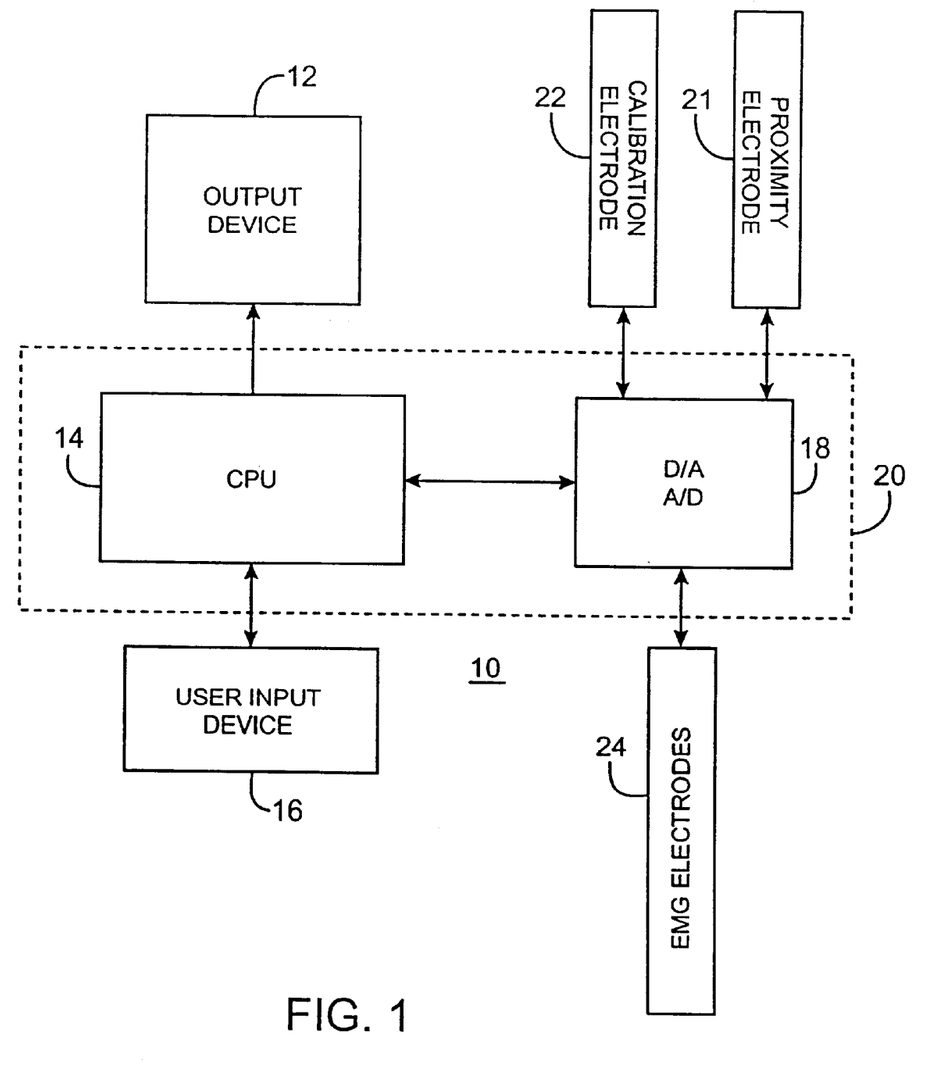
FIG. 1 is a block diagram of a nerve proximity/health detection system in accordance with the present invention.

FIG. 1 is a diagram of a nerve status and proximity system 10 in accordance with the present invention. The system 10 includes an output device 12, a user input device 16, a processor 20, a proximity electrode 21, a calibration electrode 22, and an electromyogram (EMG) electrode 24. The processor 20 includes a central processing unit ("CPU") 14 and a Digital to Analog converter ("D/A") and Analog to Digital Converter ("A/D") 18. The CPU 14 may be any microprocessor having sufficient processing power to control the operation of the D/A & A/D 18, and output device 12. The D/A & A/D 18 is any such device having a sufficient operating cycle to generate signals as described herein and a sufficient sampling rate. The calibration electrode 22 is an electrode suitable for placement near a nerve of a patient to be monitored. The EMG electrode 24 is an electrode capable of detecting an EMG response where the electrode may be inserted into a muscle physiologically coupled to a nerve to be monitored or placed on skin above the muscle. The proximity electrode 21 is an electrode that may be coupled to any medical device including a cannula, needle, catheter, RF ablation device, laser, or other medical instrument. The proximity electrode 21 may include a single electrode (mono-polar), two electrodes (bipolar), or a plurality of electrodes (multi-polar) configuration.

The CPU 14 controls the operation of the D/A & A/D 18 and output device 12 based on user selection received via the user input device 16 such as nerve proximity or status detection. The user input device 16 may be any input device including a keyboard, mouse, touch sensitive screen. The output device 12 may be any output device controllable by the CPU 14 such as computer monitor, printer, or other computer controlled display device. The system 10 generates electrical signals that are transmitted to the electrodes 21 and 22. The system interaction is described with reference to FIGS. 2 to 5. The system 10 also receives signals from EMG electrode 24. One skilled in the art is familiar with EMG electrodes and the type and format of signals received from such electrodes. In general, the system 10 generates an electrical signal for the electrodes 21 and 22 via the D/A 18. In particular, the CPU generates a digital representation of signals to be transmitted by the electrodes 21 and 22. The D/A converts the digital signals to analog signals that are transmitted by the electrodes 21 and 22. The transmitted signals are used to depolarize one or more nerves of interest located near or about the electrodes 21 and 22.

The EMG electrode 24 receives EMG or evoked muscle action potential ("EMAP") signals generated by muscle electrically coupled to the EMG electrode 24 and to a depolarized nerve (motor unit). In the present invention, the nerve is depolarized by an electrical signal transmitted by electrode 21 or 22. The A/D 18 converts the analog signal received by the EMG electrode 24 into a digital signal that may be processed by the CPU 14. The system 10 may be used to determine the proximity of the proximity electrode 21 to a nerve and status of a nerve.

Figure 2:
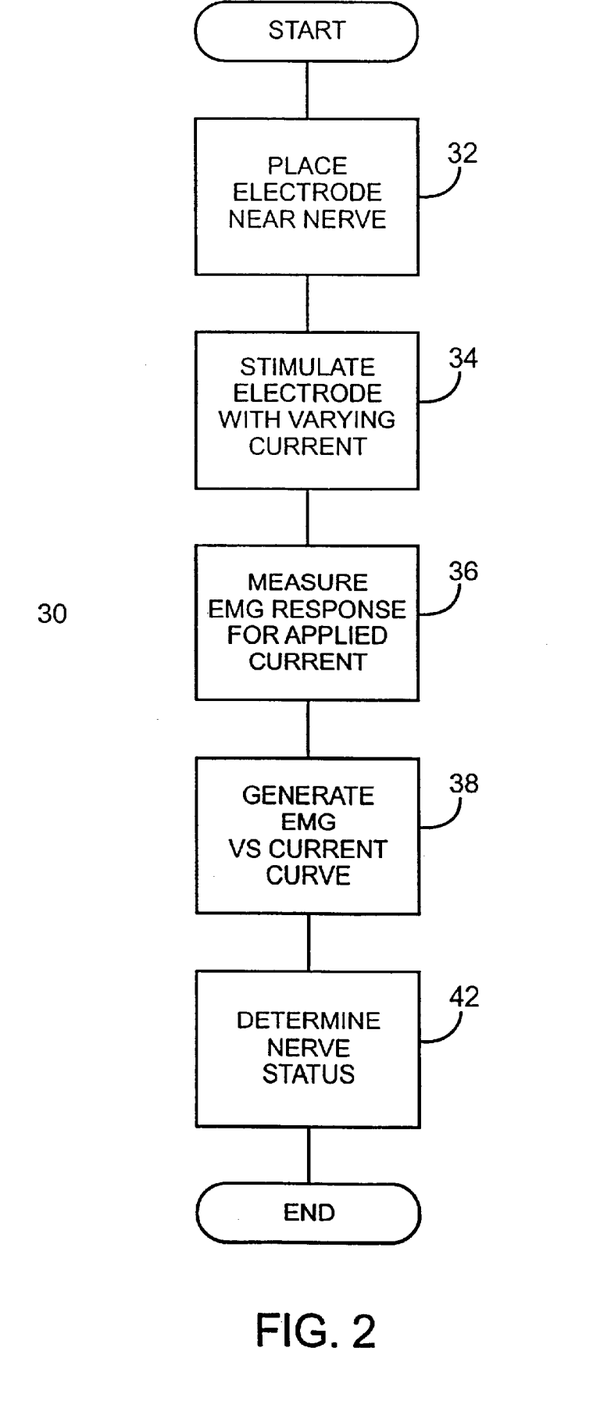
FIG. 2 is a flowchart of an exemplary method of determining nerve status in accordance with the present invention.

FIG. 2 depicts the steps of an exemplary method 30 for determining the status of a nerve. System 10 or any other capable system may perform these steps. First, at step 32, an electrode (such as electrode 21 or 22) is placed near a nerve. The nerve ideally does not move relative to the position of the electrode. Even if it moves, however, this step can be repeated at any given moment after movement has stopped. The status of a nerve may be monitored during a surgical or other medical procedure. The procedure may cause movement of the nerve at some locations. Consequently, the status electrode is positioned near a section of the nerve that is not likely to move during the procedure. For example, during lumbar surgery the status of a nerve extending from the spinal column and physiologically coupled to a muscle in a leg may be monitored. The status electrode (such as electrode 21 or 22) may be positioned midline to the nerve near the spinal column and above the surgical location. It is noted that the method will work even with other 'calibration' stimulation sites e.g., extraforaminal, which may have unwanted paraspinal muscle contractions.

The status electrode (at step 34) is stimulated with an electrical signal having a regulated current that is increased in a stepwise function over time. The voltage and initial current levels are sufficient to depolarize the nerve at the beginning of the increasing cascade of stimulation amplitude. The system 10 may be used to generate the electrical signal via the D/A converter 18. The increase in current level during each step (in time) and length of each step are determined by the latency of the response of the nerve and the depolarization threshold of the nerve. Typical stimulation values are 0 to 100 mA, with increments of 0.1 mA up to 20 mA and 1 mA increments thereafter. Voltage is variable and dependent on tissue-electrode-contact-lead impedance and is usually 0.1 V to 100 V (for an average tissue impedance of 1 kohms).

Figure 6A:
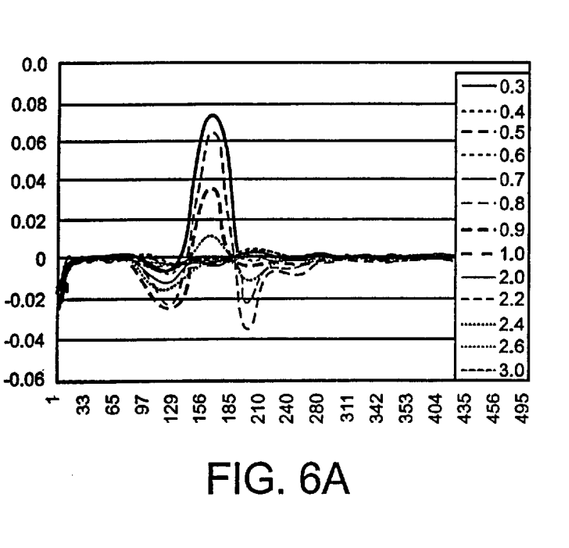
FIG. 6A is a graph depicting a plurality of EMG for different stimulation currents for an electrode placed at a calibration location relative to a nerve generating the EMG.

The response of the nerve (at step 36) is determined for each current level applied to the status electrode. In an exemplary embodiment, an EMG electrode (such as electrode 24) electrically coupled to a muscle physiologically coupled to the nerve measures the response. The response is an EMAP. EMAPs are shown in FIGS. 6A, 7A, 8A, and 9A. FIG. 6A represents EMG responses for an electrode placed near the nerve at a position relatively constant in distance to the nerve. In each FIGURE a number of EMAPs or EMG responses are shown. Each EMG response has similar characteristics, i.e., crossover points, peaks points in time and latency but the magnitude (or envelope) of the signal varies with the current applied to the electrode. Current levels that do not depolarize the nerve do not yield a measurable EMG response. As the current level is increased, the EMG response forms a repeatable pattern where only the magnitude of the peaks varies on average. Occasionally, one or more responses yield artifacts inconsistent with other responses. Ideally, these artifacts are discarded. As the current level is increased the magnitude of the peaks of the EMG responses continues to increase until a point of nerve saturation is reached. At this point increasing the current level of the signal applied to the electrode (and thus to the nerve) will not increase the magnitude of the peaks of the EMG responses. The current levels of the signal applied the status electrode ideally stop at or before the saturation point of the nerve.

Figure 4:
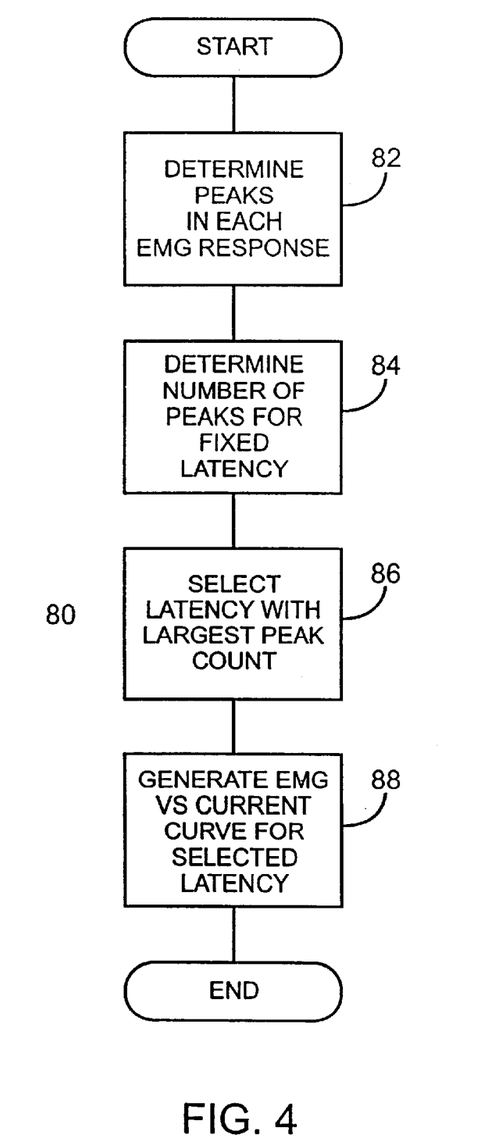
FIG. 4 is a flowchart of a first exemplary method of generating an EMG response versus current curve in accordance with the present invention.
Figure 5:
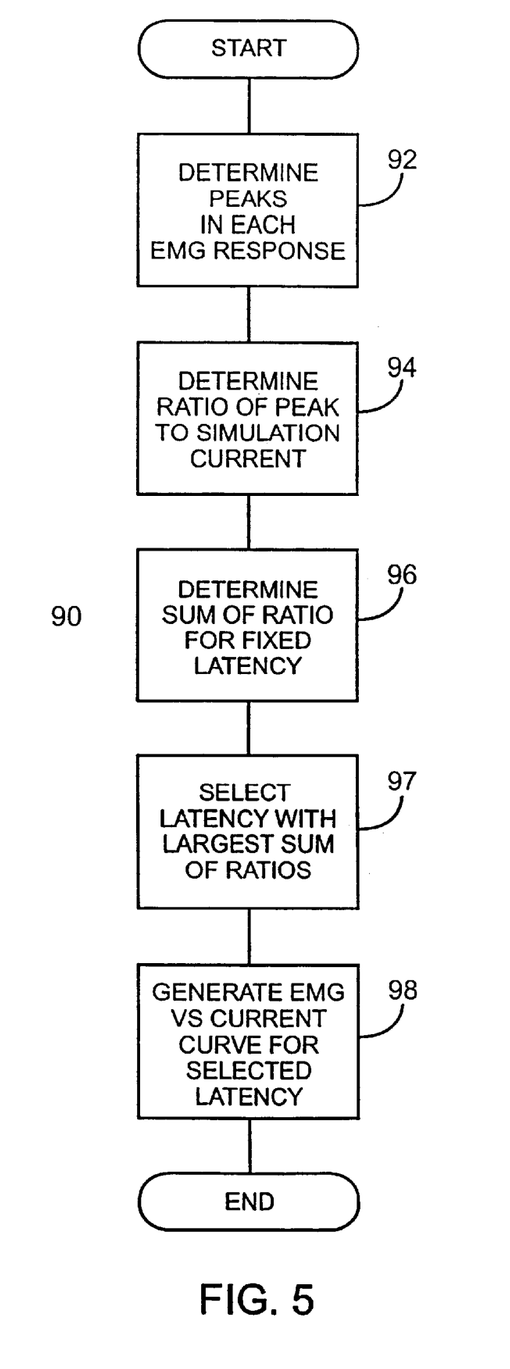
FIG. 5 is a flowchart of a second exemplary method of generating an EMG response versus current curve in accordance with the present invention.
Figure 6B:
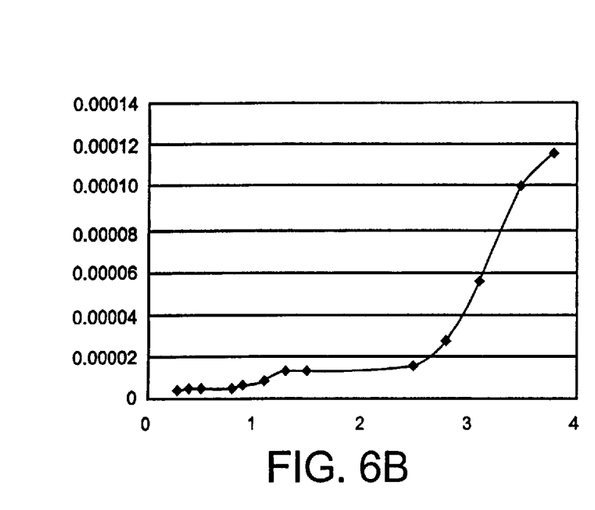
FIG. 6B is a graph depicting an EMG response versus stimulation current for a selected fixed latency generated from the graph shown in FIG. 6A.

A mapping of the EMG response versus the applied current (at step 38) is generated for a selected point in time or fixed latency of the EMG responses. Mapped responses of EMG response versus applied current are shown in FIGS. 6B, 7B, 8B, and 9B. FIG. 6B represents the EMG response versus applied current level for an electrode placed near the nerve at a position relatively constant in distance to the nerve. As can be seen in FIG. 6A, the mapping of EMG response to applied current level is ideally determined at a time point or latency of the EMG response that has measurable variability. FIGS. 4 and 5 depict two different exemplary methods of selecting the latency or time point to be used to map the EMG response to the applied current level and generating the EMG response versus applied current levels.

Method 80 depicted in FIG. 4 first determines the peaks in each EMG or EMAP response at step 82. In particular, the method determines the latency or time point in each response that has the largest magnitude. Then the method determines how many other responses have approximately the same maximum magnitude latency at step 84 for each determined peak latency. The latency having the largest number of maximum magnitude peaks is selected as the fixed latency or time period in step 86. The fixed latency or time period is then used to generate the EMG response versus applied current level mapping in step 88.

In method 90, the EMG response versus applied current level mapping is also generated for a selected time period or latency. The latency is determined in similar manner. The method 90 determines the maximum magnitude peak in each EMG or EMAP response at step 92. The method then determines the ratio of the peak to the stimulation current for the EMG curve, i.e., a weighted peak at step 94. Then the method determines the sum of the weighted peaks for all the responses have approximately the same peak latency at step 96. The latency having the largest sum of weighted peaks is selected as the fixed latency or time period in step 97. The fixed latency or time period is then used to generate the EMG response versus applied current level mapping in step 98.

Having mapped the EMG response to applied current levels, the method 30 determines the nerve status at step 42 based on the mapping. In an exemplary embodiment, the method determines the slope of the mapping. When the slope (dV/dI) is going toward infinity (parallel to the y-axis in µV), the nerve status is considered healthy. Otherwise with decreased slope, ultimately going towards zero or the x-axis (mA) the nerve status is considered unhealthy. This only applies for the stimulation electrode in close proximity of the neuron. In another embodiment, the mapping may be compared to mappings for healthy and unhealthy nerves. Correlating the mappings respectively may perform the comparison. The result of the nerve status determination may be displayed on output device 12. In addition, the determination may be performed periodically during a medical procedure to access the success of the procedure.

Figure 3:
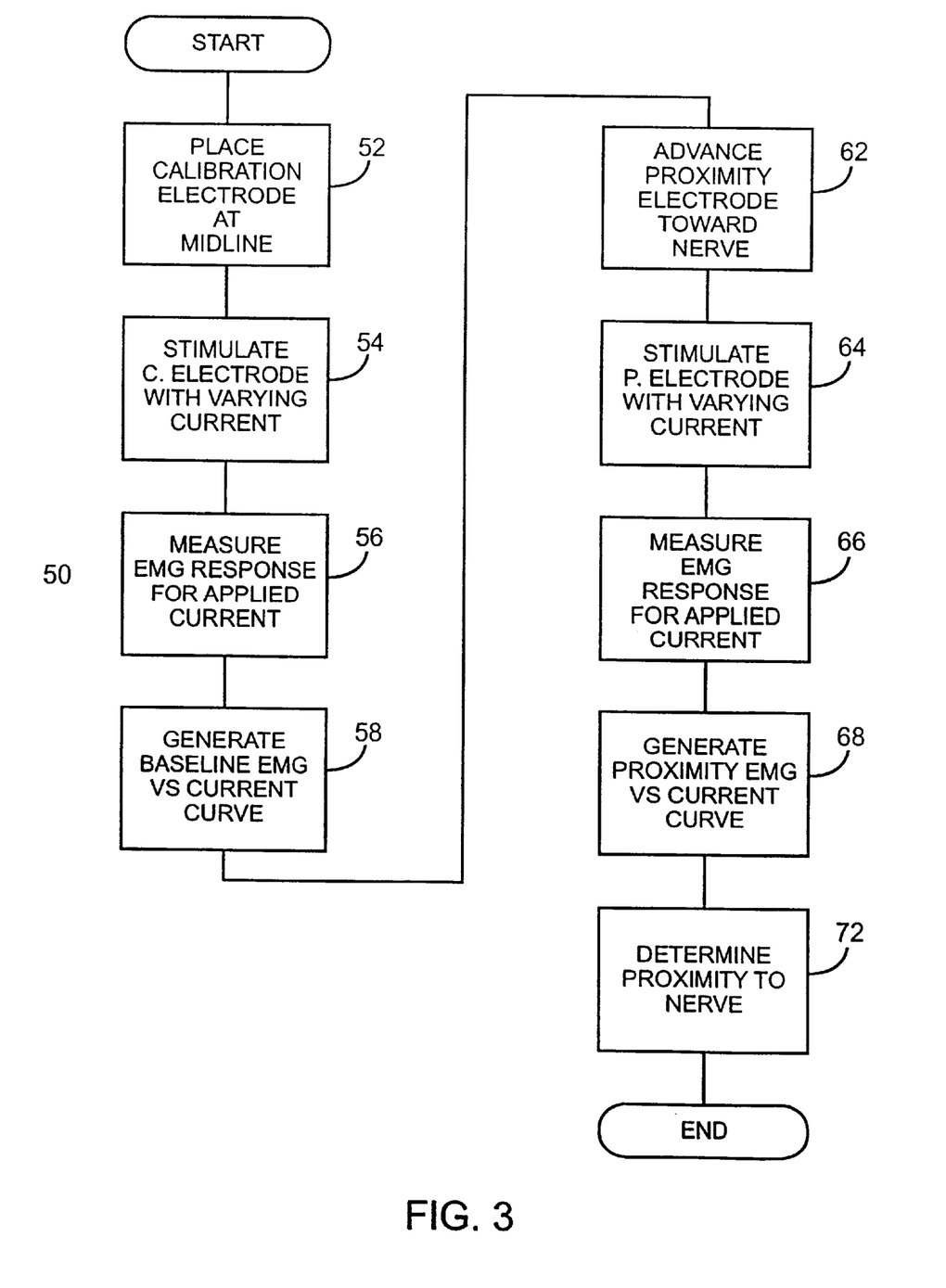
FIG. 3 is a flowchart of an exemplary method of determining nerve proximity in accordance with the present invention.

The present invention also includes a method for determining the proximity of a nerve to a conductive element (such as proximity electrode 21). An exemplary method for determining the proximity of a nerve to a conductive element is depicted in FIG. 3. In this method a mapping of calibration EMG response versus applied current level is determined for a calibration electrode located at a known distance from a nerve. Then a mapping of EMG response versus applied current level is determined for the proximity electrode. Based on the differences between the two mappings, the relative proximity of the nerve to the proximity electrode is determined. In detail, a calibration electrode is placed at a location near the nerve where the distance from the nerve to the calibration electrode is known and ideally fixed (at step 52.). In one embodiment, the calibration electrode is placed in the epidural space above the dura of the spinal column. The calibration electrode is placed between the spinous process near the nerve of interest and midline to the spinal column. In one embodiment, the proximity is derived from the change in current (delta mA) of the two mappings and the relative slope comparison of both. Proximity can be derived from just one measurement compared to the calibration curve, however the probability safety increases with multiple readings.

Figure 7A:
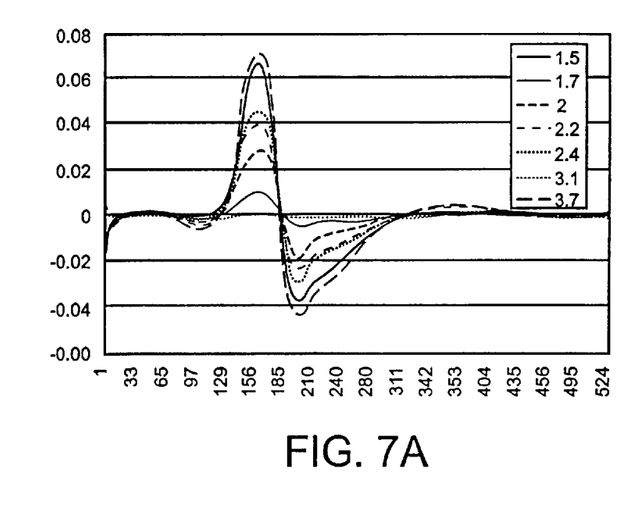
FIG. 7A is a graph depicting a plurality of EMG for different stimulation currents for an electrode placed directly adjacent to a nerve generating the EMG.
Figure 7B:
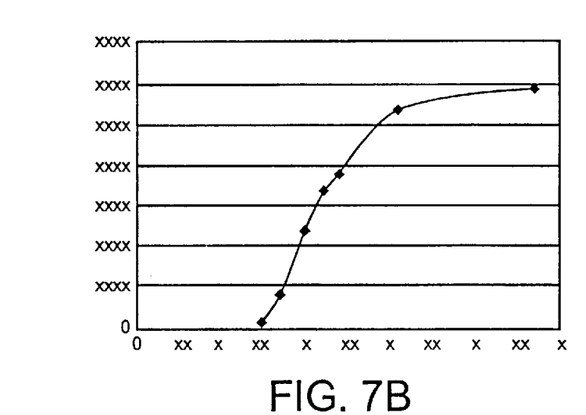
FIG. 7B is a graph depicting an EMG response versus stimulation current for a selected fixed latency generated from the graph shown in FIG. 7A.
Figure 8A:
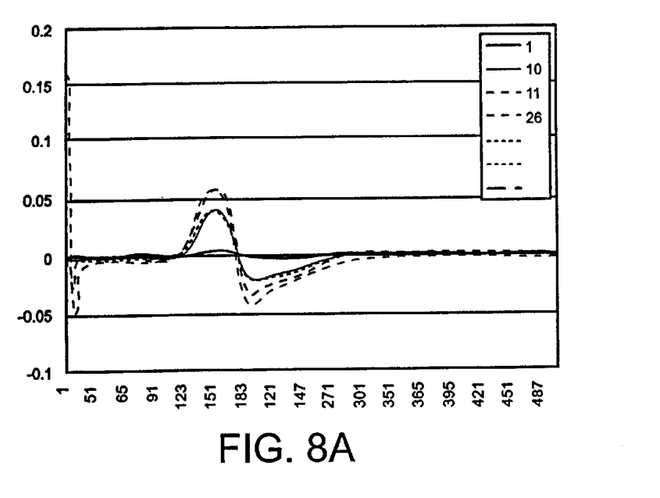
FIG. 8A is a graph depicting a plurality of EMG for different stimulation currents for an electrode placed about 10 mm from a nerve generating the EMG.
Figure 8B:
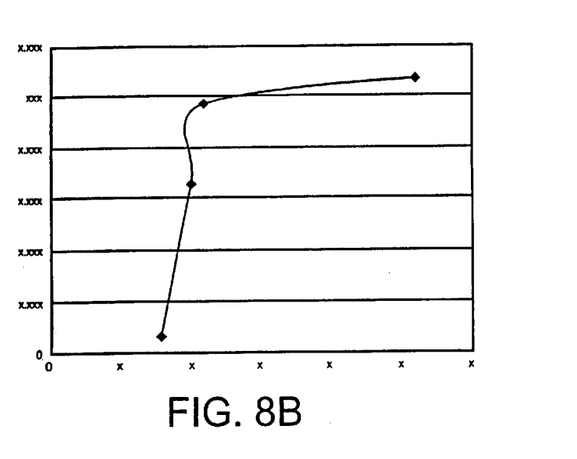
FIG. 8B is a graph depicting an EMG response versus stimulation current for a selected fixed latency generated from the graph shown in FIG. 8A.
Figure 9A:
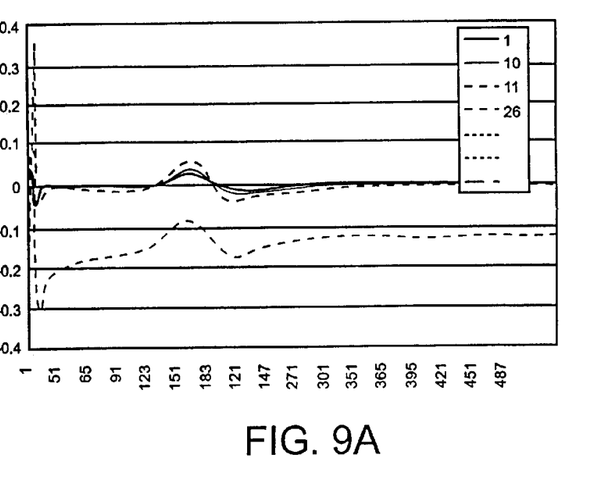
FIG. 9A is a graph depicting a plurality of EMG for different stimulation currents for an electrode placed about 20 mm from a nerve generating the EMG.
Figure 9B:
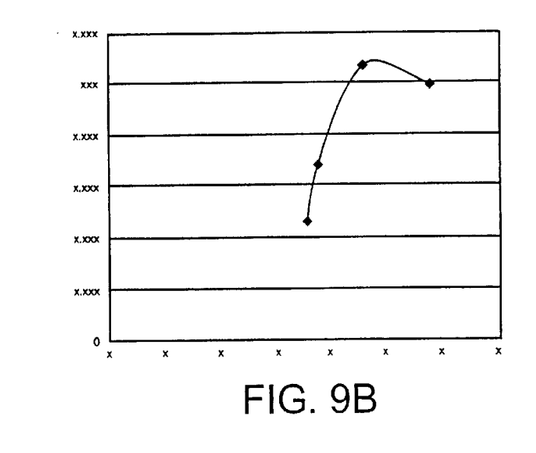
FIG. 9B is a graph depicting an EMG response versus stimulation current for a selected fixed latency generated from the graph shown in FIG. 9A.
Figure 10:
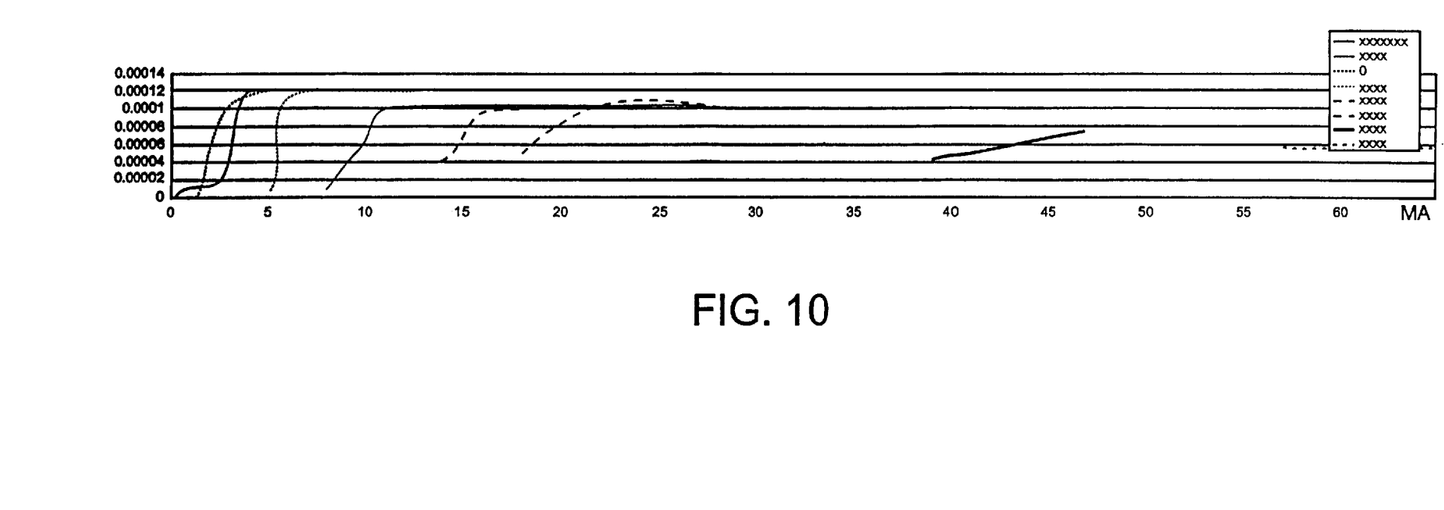
FIG. 10 is a graph depicting a plurality of EMG responses versus stimulation current levels for a selected fixed latency for electrodes placed at varying distances from the nerve generating the EMG responses.

In steps 54, 56, and 58, the mapping of EMG response versus applied current level is determined. FIG. 6B represents the mapping for a calibration electrode placed substantially adjacent to a nerve. This curve is also shown in FIG. 10 with a start point of about 0 mA (milliamperes). Then after placing the proximity electrode at a desired location at step 62, the mapping of the EMG response versus applied current level is determined at steps 64, 66, and 68 for the proximity electrode. The two mappings (for the calibration electrode and proximity electrode) are then compared. In an exemplary embodiment, the offset in current (mA) between the two mappings is compared and used to determine the relative proximity of the proximity electrode to the nerve. For example, FIG. 7B depicts the mapping of a proximity electrode directly adjacent to a nerve (FIG. 7A is the EMAP responses for each current level). FIG. 8B depicts the mapping of a proximity electrode located about 10 mm from the nerve (FIG. 8A is the EMAP responses for each current level). FIG. 9B depicts the mapping of a proximity electrode located about 20 mm from the nerve (FIG. 9A is the EMAP responses for each current level).

FIG. 10 shows mappings on the same chart for electrodes located at 0 mm, calibration position, 5 mm, 10 mm, 15 mm, 20 mm, 25 mm, and 30 mm from the nerve. As can be seen from this FIGURE, as the proximity electrode moves further from the nerve the slope of the mapping decreases and the mapping is offset further in current (mA). Accordingly, the method, at step 72, may determine distance from the nerve using the calibration mapping and proximity mapping. It is noted that the mapping may only have one or more points where the nerve is depolarized and still provide accurate ranging or proximity information.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution.

As can be envisioned by one of skill in the art, many different combinations of the above may be used and accordingly the present invention is not limited by the scope of the appended claims.

What is claimed is:

1. A method of determining nerve status comprising the steps of:
   (a) applying an electrical signal having a plurality of predetermined current levels to a conductive element located near the nerve;
   (b) measuring the responses of the nerve to the applied electrical signal for the plurality of predetermined current levels;
   (c) mapping the responses of the nerve to the applied electrical signal for the plurality of predetermined current levels; and
   (d) determining the nerve status based on an interpretation of the mapped responses of the nerve to the applied electrical signal for the plurality of predetermined current levels.

2. The method of claim 1, wherein step c) includes mapping the responses of the nerve to the applied electrical signal for the plurality of predetermined current levels for a fixed latency, and wherein step d) includes determining the nerve status based on the mapping of the responses of the nerve to the applied electrical signal for the plurality of predetermined current levels for the fixed latency.

3. The method of claim 2, wherein step a) includes placing a conductive element near the nerve, and applying an electrical signal having a plurality of predetermined current levels to the conductive element.

4. The method of claim 3, wherein step a) includes placing a conductive element in the epidural space above the dura of the spinal column in which the nerve is located.

5. The method of claim 2, wherein each response is an EMG.

6. The method of claim 2, wherein each response is an EMG measured at a muscle physiologically coupled to the nerve.

7. The method of claim 1, wherein step d) of determining nerve status is based on an interpretation of the slope of the mapped responses of the nerve to the applied electrical signal for the plurality of predetermined current levels.

8. The method of claim 1, wherein step d) of determining nerve status is based on an interpretation of a comparison between the mapped responses of the nerve to the applied electrical signal for the plurality of predetermined current levels and known mappings for at least one of healthy and unhealthy nerves.

9. The method of claim 1, wherein step d) of determining nerve status is performed to assess the effect of a surgical procedure on nerve status.

10. The method of claim 1, wherein step d) of determining nerve status is performed intraoperatively to assess the effect of a surgical procedure on nerve status.

11. The method of claim 1, wherein the conductive element is coupled to a medical device.

12. The method of claim 11, wherein the medical device comprises at least one of a cannula, a catheter, and a needle.

13. The method of claim 1, wherein each response is an EMG.

14. The method of claim 1, wherein each response is an EMG measured at a muscle physiologically coupled to the nerve.

15. A method of determining nerve status comprising the steps of:
   (a) applying an electrical signal having a plurality of predetermined current levels to a conductive element located near the nerve;
   (b) measuring the responses of the nerve to the applied electrical signal for the plurality of predetermined current levels; and
   (c) determining the nerve status based on the responses of the nerve to the applied electrical signal for the plurality of predetermined current levels, including the sub-steps of (i) mapping the responses of the nerve to the applied electrical signal for the plurality of predetermined current levels for a fixed latency; and (ii) determining the nerve status based on the mapping of the responses of the nerve to the applied electrical signal for the plurality of predetermined current levels for the fixed latency, wherein the fixed latency is a function of peaks in each response of the nerve to the applied electrical signal for the plurality of predetermined current levels.

16. The method of claim 15, wherein the fixed latency is selected by performing the steps of:
   (a) determining the peaks in the responses of the nerve to the applied electrical signal for the plurality of predetermined current levels; and
   (b) selecting the latency having the largest number of peaks located thereabout.

17. The method of claim 15, wherein the fixed latency is selected by performing the steps of:
   (a) determining the peaks in the responses of the nerve to the applied electrical signal for the plurality of predetermined current levels;
   (b) determining the number of peaks located about each latency having a peak located thereabout; and
   (c) selecting the latency having the largest number of peaks located thereabout.

18. The method of claim 15, wherein the fixed latency is selected by performing the steps of:
   (a) determining the peaks in the responses of the nerve to the applied electrical signal for the plurality of predetermined current levels;
   (b) determining the ratio of the peak level to corresponding current level for each peak;

(c) determining the sum of the ratio of peak level to current level for peaks located about each latency having a peak located thereabout; and (d) selecting the latency having the largest sum of ratios.

19. The method of claim 18, wherein each response is an EMG.

20. The method of claim 18, wherein each response is an EMG measured at a muscle physiologically coupled to the nerve.

21. An article of manufacture for use in determining nerve status, the article of manufacture comprising computer readable storage media including program logic embedded therein that causes control circuitry to perform the steps of:

(a) applying an electrical signal having a plurality of predetermined current levels to a conductive element located near the nerve;

(b) measuring the responses of the nerve to the applied electrical signal for the plurality of predetermined current levels;

(c) mapping the responses of the nerve to the applied electrical signal for the plurality of predetermined current levels; and (d) determining the nerve status based on an interpretation of the mapped responses of the nerve to the applied electrical signal for the plurality of predetermined current levels.

22. The article of manufacture for use in determining nerve status of claim 21, wherein step c) includes mapping the responses of the nerve to the applied electrical signal for the plurality of predetermined current levels for a fixed latency, and wherein step d) includes determining the nerve status based on the mapping of the responses of the nerve to the applied electrical signal for the plurality of predetermined current levels for the fixed latency.

23. The article of manufacture for use in determining nerve status of claim 12, wherein each response is an EMG.

24. The article of manufacture for use in determining nerve status of claim 21, wherein each response is an EMG measured at a muscle physiologically coupled to the nerve.

25. The article of manufacture of claim 21, wherein step d) of determining nerve status is based on an interpretation of the slope of the mapped responses of the nerve to the applied electrical signal for the plurality of predetermined current levels.

26. The article of manufacture of claim 21, wherein step d) of determining nerve status is based on an interpretation of a comparison between the mapped responses of the nerve to the applied electrical signal for the plurality of predetermined current levels and known mappings for at least one of healthy and unhealthy nerves.

27. The article of manufacture of claim 21, wherein step d) of determining nerve status is performed to assess the effect of a surgical procedure on nerve status.

28. The article of manufacture of claim 21, wherein step d) of determining nerve status is performed intraoperatively to assess the effect of a surgical procedure on nerve status.

29. The article of manufacture of claim 21, wherein the conductive element is coupled to a medical device.

30. The article of manufacture of claim 29, wherein the medical device comprises at least one of a cannula, a catheter, and a needle.

31. The article of manufacture of claim 21, wherein each response is an EMG.

32. The article of manufacture of claim 21, wherein each response is an EMG measured at a muscle physiologically coupled to the nerve.

33. An article of manufacture for use in determining nerve status, the article of manufacture comprising computer readable storage media including program logic embedded therein that causes control circuitry to perform the steps of:

(a) applying an electrical signal having a plurality of predetermined current levels to a conductive element located near the nerve;

(b) measuring the responses of the nerve to the applied electrical signal for the plurality of predetermined current levels; and (c) determining the nerve status based on the responses of the nerve to the applied electrical signal for the plurality of predetermined current levels, including the substeps of (i) mapping the responses of the nerve to the applied electrical signal for the plurality of predetermined current levels for a fixed latency; and (ii) determining the nerve status based on the mapping of the responses of the nerve to the applied electrical signal for the plurality of predetermined current levels for the fixed latency, wherein the fixed latency is a function of peaks in each response of the nerve to the applied electrical signal for the plurality of predetermined current levels.

34. The article of manufacture for use in determining nerve status of claim 33, wherein the fixed latency is selected by performing the steps of:

(a) determining the peaks in the responses of the nerve to the applied electrical signal for the plurality of predetermined current levels; and (b) selecting the latency having the largest number of peaks located thereabout.

35. The article of manufacture for use in determining nerve status of claim 33, herein the fixed latency is selected by performing the steps of:

(a) determining the peaks in the responses of the nerve to the applied electrical signal for the plurality of predetermined current levels;

(b) determining the number of peaks located about each latency having a peak located thereabout; and (c) selecting the latency having the largest number of peaks located thereabout.

36. The article of manufacture for use in determining nerve status of claim 33, wherein the fixed latency is selected by performing the steps of:

(a) determining the peaks in the responses of the nerve to the applied electrical signal for the plurality of predetermined current levels;

(b) determining the ratio of the peak level to corresponding current level for each peak;

(c) determining the sum of the ratio of peak level to current level for peaks located about each latency having a peak located thereabout; and (d) selecting the latency having the largest sum of ratios.

37. An apparatus for determining nerve status, the apparatus comprising:

(a) means for applying an electrical signal having a plurality of predetermined current levels to a conductive element located near the nerve;

(b) means for measuring the responses of the nerve to the applied electrical signal for the plurality of predetermined current levels;

(c) means for mapping the responses of the nerve to the applied electrical signal for the plurality of predetermined current levels; and (d) means for determining the nerve status based on an interpretation of the mapped responses of the nerve to the applied electrical signal for the plurality of predetermined current levels.

38. The apparatus of claim 37, wherein the means for mapping the responses of the nerve to the applied electrical signal for the plurality of predetermined current levels includes means for mapping the responses of the nerve to the applied electrical signal for the plurality of predetermined current levels for a fixed latency.

39. The apparatus of claim 38, wherein each response is an EMG.

40. The apparatus of claim 21, wherein each response is an EMG measured at a muscle physiologically coupled to the nerve.

41. The apparatus of claim 31, wherein the determination of nerve status is based on an interpretation of the slope of the mapped responses of the nerve to the applied electrical signal for the plurality of predetermined current levels.

42. The apparatus of claim 37, herein the determination of nerve status is based on an interpretation of a comparison between the mapped responses of the nerve to the applied electrical signal for the plurality of predetermined current levels and known mappings for at least one of healthy and unhealthy nerves.

43. The apparatus of claim 37, wherein the determination of nerve status is performed to assess the effect of a surgical procedure on nerve status.

44. The apparatus of claim 37, wherein the determination of nerve status is performed intraoperatively to assess the effect of a surgical procedure on nerve status.

45. The apparatus of claim 37, wherein the conductive element is coupled to a medical device.

46. The apparatus of claim 45, wherein the medical device comprises at least one of a cannula, a catheter, and a needle.

47. The apparatus of claim 20, wherein each response is an EMG.

48. The apparatus of claim 37, wherein each response is an EMG measured at a muscle physiologically coupled to the nerve.

49. An apparatus for determining nerve status, the apparatus comprising:
(a) means for applying an electrical signal having a plurality of predetermined current levels to a conductive element located near the nerve;
(b) means for measuring the responses of the nerve to the applied electrical signal for the plurality of predetermined current levels; and
(c) means for determining the nerve status based on the responses of the nerve to the applied electrical signal for the plurality of predetermined current levels, including (i) means for mapping the responses of the nerve to the applied electrical signal for the plurality of predetermined current levels for a fixed latency, (ii) means for determining the nerve status based on the mapping of the responses of the nerve to the applied electrical signal for the plurality of predetermined current levels for the fixed latency, and (iii) means for determining the fixed latency as a function of peaks in each response of the nerve to the applied electrical signal for the plurality of predetermined current levels.

50. The apparatus of claim 49, further comprising:
(a) means for determining the peaks in the responses of the nerve to the applied electrical signal for the plurality of predetermined current levels; and
(b) means for selecting the latency having the largest number of peaks located thereabout as the fixed latency.

51. The apparatus of claim 49, further comprising:
(a) means for determining the peaks in the responses of the nerve to the applied electrical signal for the plurality of predetermined current levels;
(b) means for determining the number of peaks located about each latency having a peak located thereabout; and
(c) means for selecting the latency having the largest number of peaks located thereabout as the fixed latency.

52. The apparatus of claim 49, further comprising:
(a) means for determining the peaks in the responses of the nerve to the applied electrical signal for the plurality of predetermined current levels;
(b) means for determining the ratio of the peak level to corresponding current level for each peak;
(c) means for determining the sum of the ratio of peak level to current level for peaks located about each latency having a peak located thereabout; and
(d) means for selecting the latency having the largest sum of ratios as the fixed latency.

53. The apparatus of claim 52, wherein each response is an EMG.

54. The apparatus of claim 52, wherein each response is an EMG measured at a muscle physiologically coupled to the nerve.

55. A method of determining proximity of a nerve to a second conductive element comprising the steps of:
(a) applying a first electrical signal having a plurality of predetermined current levels to a first conductive element located near the nerve;
(b) measuring the responses of the nerve to the first applied electrical signal for the plurality of predetermined current levels;
(c) applying a second electrical signal having the plurality of predetermined current levels to the second conductive element;
(d) measuring the responses of the nerve to the second applied electrical signal for the plurality of predetermined current levels; and
(e) determining the nerve proximity to the second conductive element based on the responses of the nerve to the first applied electrical signal for the plurality of predetermined current levels relative to the responses of the nerve to the second applied electrical signal for the plurality of predetermined current levels.

56. The method of claim 55, wherein step e) includes:
(a) mapping the responses of the nerve to the first applied electrical signal for the plurality of predetermined current levels for a first fixed latency;
(b) mapping of the responses of the nerve to the second applied electrical signal for the plurality of predetermined current levels for a second fixed latency and
(c) determining the nerve proximity to the second conductive element based on the mapping of the responses of the nerve to the first applied electrical signal for the plurality of predetermined current levels for the first fixed latency and the mapping of the responses of the nerve to the second applied electrical signal for the plurality of predetermined current levels for the second fixed latency.

57. The method of claim 56, wherein step a) includes:
(a) placing a first conductive element near the nerve; and
(b) applying a first electrical signal having a plurality of predetermined current levels to the first conductive element.

58. The method of claim 30, wherein each response is an EMG.

59. The method of claim 55, wherein each response is an EMG measured at a muscle physiologically coupled to the nerve.

60. A method of determining proximity of a nerve to a second conductive element comprising the steps of:
  (a) applying a first electrical signal having a plurality of predetermined current levels to a first conductive element located near the nerve;
  (b) measuring the responses of the nerve to the first applied electrical signal for the plurality of predetermined current levels;
  (c) applying a second electrical signal having the plurality of predetermined current levels to the second conductive element;
  (d) measuring the responses of the nerve to the second applied electrical signal for the plurality of predetermined current levels; and
  (e) determining the nerve proximity to the second conductive element based on the responses of the nerve to the first applied electrical signal for the plurality of predetermined current levels and the responses of the nerve to the second applied electrical signal for the plurality of predetermined current levels, including the sub-steps of: (i) mapping the responses of the nerve to the first applied electrical signal for the plurality of predetermined current levels for a first fixed latency; (ii) mapping of the responses of the nerve to the second applied electrical signal for the plurality of predetermined current levels for a second fixed latency; (iii) determining the nerve proximity to the second conductive element based on the mapping of the responses of the nerve to the first applied electrical signal for the plurality of predetermined current levels for the first fixed latency and the mapping of the responses of the nerve to the second applied electrical signal for the plurality of predetermined current levels for the second fixed latency; and (iv) determining the first fixed latency as a function of peaks in each response of the nerve to the first applied electrical signal for the plurality of predetermined current levels.

61. The method of claim 60, wherein the first fixed latency is selected by performing the steps of:
  (a) determining the peaks in the responses of the nerve to the first applied electrical signal for the plurality of predetermined current levels; and
  (b) selecting the latency having the largest number of peaks located thereabout as the first fixed latency.

62. The method of claim 60, wherein the first fixed latency is selected by performing the steps of:
  (a) determining the peaks in the responses of the nerve to the first applied electrical signal for the plurality of predetermined current levels;
  (b) determining the number of peaks located about each latency having a peak located thereabout; and
  (c) selecting the latency having the largest number of peaks located thereabout as the first fixed latency.

63. The method of claim 60, wherein the first fixed latency is selected by performing the steps of:
  (a) determining the peaks in the responses of the nerve to the first applied electrical signal for the plurality of predetermined current levels;
  (b) determining the ratio of the peak level to corresponding current level for each peak;
  (c) determining the sum of the ratio of peak level to current level for peaks located about each latency having a peak located thereabout; and
  (d) selecting the latency having the largest sum of ratios as the first fixed latency.

64. The method of claim 63, wherein each response is an EMG.

65. The method of claim 63, wherein each response is an EMG measured at a muscle physiologically coupled to the nerve.

66. The method of claim 65, wherein the second fixed latency is equal to the first fixed latency.

67. An article of manufacture for use in determining proximity of a nerve to a second conductive element, the article of manufacture comprising computer readable storage media including program logic embedded therein that causes control circuitry to perform the steps of:
  (a) applying a first electrical signal having a plurality of predetermined current levels to a first conductive element located near the nerve;
  (b) measuring the responses of the nerve to the first applied electrical signal for the plurality of predetermined current levels;
  (c) applying a second electrical signal having the plurality of predetermined current levels to the second conductive element;
  (d) measuring the responses of the nerve to the second applied electrical signal for the plurality of predetermined current levels; and
  (e) determining the nerve proximity to the second conductive element based on the responses of the nerve to the first applied electrical signal for the plurality of predetermined current levels relative to the responses of the nerve to the second applied electrical signal for the plurality of predetermined current levels.

68. The article of manufacture for use in determining proximity of a nerve to a second conductive element of claim 67, wherein step e) includes:
  (a) mapping the responses of the nerve to the first applied electrical signal for the plurality of predetermined current levels for a first fixed latency;
  (b) mapping the responses of the nerve to the second applied electrical signal for the plurality of predetermined current levels for a second fixed latency and
  (c) determining the nerve proximity to the second conductive element based on the mapping of the responses of the nerve to the first applied electrical signal for the plurality of predetermined current levels for the first fixed latency and the mapping of the responses of the nerve to the second applied electrical signal for the plurality of predetermined current levels for the second fixed latency.

69. The article of manufacture for use in determining proximity of a nerve to a second conductive element of claim 67, wherein each response is an EMG.

70. The article of manufacture for use in determining proximity of a nerve to a second conductive element of claim 67, each response is an EMG measured at a muscle physiologically coupled to the nerve.

71. An article of manufacture for use in determining proximity of a nerve to a second conductive element, the article of manufacture comprising computer readable storage media including program logic embedded therein that causes control circuitry to perform the steps of:
  (a) applying a first electrical signal having a plurality of predetermined current levels to a first conductive element located near the nerve;

(b) measuring the responses of the nerve to the first applied electrical signal for the plurality of predetermined current levels;

(c) applying a second electrical signal having the plurality of predetermined current levels to the second conductive element;

(d) measuring the responses of the nerve to the second applied electrical signal for the plurality of predetermined current levels; and (e) determining the nerve proximity to the second conductive element based on the responses of the nerve to the first applied electrical signal for the plurality of predetermined current levels and the responses of the nerve to the second applied electrical signal for the plurality of predetermined current levels, including the sub-steps of: (i) mapping the responses of the nerve to the first applied electrical signal for the plurality of predetermined current levels for a first fixed latency; (ii) mapping the responses of the nerve to the second applied electrical signal for the plurality of predetermined current levels for a second fixed latency; (iii) determining the nerve proximity to the second conductive element based on the mapping of the responses of the nerve to the first applied electrical signal for the plurality of predetermined current levels for the first fixed latency and the mapping of the responses of the nerve to the second applied electrical signal for the plurality of predetermined current levels for the second fixed latency; and (iv) determining the first fixed latency as a function of peaks in each response of the nerve to the first applied electrical signal for the plurality of predetermined current levels.

72. The article of manufacture for use in determining proximity of a nerve to a second conductive element of claim 71, wherein the first fixed latency is selected by performing the steps of:

(a) determining the peaks in the responses of the nerve to the first applied electrical signal for the plurality of predetermined current levels; and (b) selecting the latency having the largest number of peaks located thereabout as the first fixed latency.

73. The article of manufacture for use in determining proximity of a nerve to a second conductive element of claim 71, wherein the first fixed latency is selected by performing the steps of:

(a) determining the peaks in the responses of the nerve to the first applied electrical signal for the plurality of predetermined current levels;

(b) determining the number of peaks located about each latency having a peak located thereabout; and (c) selecting the latency having the largest number of peaks located thereabout as the first fixed latency.

74. The article of manufacture for use in determining proximity of a nerve to a second conductive element of claim 71, wherein the first fixed latency is selected by performing the steps of:

(a) determining the peaks in the responses of the nerve to the first applied electrical signal for the plurality of predetermined current levels;

(b) determining the ratio of the peak level to corresponding current level for each peak;

(c) determining the sum of the ratio of peak level to current level for peaks located about each latency having a peak located thereabout; and (d) selecting the latency having the largest sum of ratios as the first fixed latency.

75. The article of manufacture for use in determining proximity of a nerve to a second conductive element of claim 74, wherein each response is an EMG.

76. The article of manufacture for use in determining proximity of a nerve to a second conductive element of claim 74, wherein each response is an EMG measured at a muscle physiologically coupled to the nerve.

77. The article of manufacture for use in determining proximity of a nerve to a second conductive element of claim 76, wherein the second fixed latency is equal to the first fixed latency.

78. An apparatus for determining proximity of a nerve to a second conductive element, the apparatus comprising:

(a) means for applying a first electrical signal having a plurality of predetermined current levels to a first conductive element located near the nerve;

(b) means for measuring the responses of the nerve to the first applied electrical signal for the plurality of predetermined current levels;

(c) means for applying a second electrical signal having the plurality of predetermined current levels to the second conductive element;

(d) means for measuring the responses of the nerve to the second applied electrical signal for the plurality of predetermined current levels; and (e) means for determining the nerve proximity to the second conductive element based on the responses of the nerve to the first applied electrical signal for the plurality of predetermined current levels relative to the responses of the nerve to the second applied electrical signal for the plurality of predetermined current levels.

79. The apparatus for determining proximity of a nerve to a second conductive element of claim 78, wherein the means for determining the nerve proximity to the second conductive element includes:

(a) means for mapping the responses of the nerve to the first applied electrical signal for the plurality of predetermined current levels for a first fixed latency;

(b) means for mapping the responses of the nerve to the second applied electrical signal for the plurality of predetermined current levels for a second fixed latency and (c) means for determining the nerve proximity to the second conductive element based on the mapping of the responses of the nerve to the first applied electrical signal for the plurality of predetermined current levels for the first fixed latency and the mapping of the responses of the nerve to the second applied electrical signal for the plurality of predetermined current levels for the second fixed latency.

80. The apparatus for determining proximity of a nerve to a second conductive element of claim 78, wherein each response is an EMG.

81. The apparatus for determining proximity of a nerve to a second conductive element of claim 78, wherein each response is an EMG measured at a muscle physiologically coupled to the nerve.

82. An apparatus for determining proximity of a nerve to a second conductive element, the apparatus comprising:

(a) means for applying a first electrical signal having a plurality of predetermined current levels to a first conductive element located near the nerve;

(b) means for measuring the responses of the nerve to the first applied electrical signal for the plurality of predetermined current levels;

(c) means for applying a second electrical signal having the plurality of predetermined current levels to the second conductive element;

(d) means for measuring the responses of the nerve to the second applied electrical signal for the plurality of predetermined current levels; and (e) means for determining the nerve proximity to the second conductive element based on the responses of the nerve to the first applied electrical signal for the plurality of predetermined current levels and the responses of the nerve to the second applied electrical signal for the plurality of predetermined current levels, including: (i) means for mapping the responses of the nerve to the first applied electrical signal for the plurality of predetermined current levels for a first fixed latency; (ii) means for mapping the responses of the nerve to the second applied electrical signal for the plurality of predetermined current levels for a second fixed latency; (iii) means for determining the nerve proximity to the second conductive element based on the mapping of the responses of the nerve to the first applied electrical signal for the plurality of predetermined current levels for the first fixed latency and the mapping of the responses of the nerve to the second applied electrical signal for the plurality of predetermined current levels for the second fixed latency; and (iv) means for determining the first fixed latency as a function of peaks in each response of the nerve to the first applied electrical signal for the plurality of predetermined current levels.

83. The apparatus for determining proximity of a nerve to a second conductive element of claim 82, further comprising:

(a) means for determining the peaks in the responses of the nerve to the first applied electrical signal for the plurality of predetermined current levels; and (b) means for selecting the latency having the largest number of peaks located thereabout as the first fixed latency.

84. The apparatus for determining proximity of a nerve to a second conductive element of claim 82, further comprising:

(a) means for determining the peaks in the responses of the nerve to the first applied electrical signal for the plurality of predetermined current levels;

(b) means for determining the number of peaks located about each latency having a peak located thereabout; and (c) means for selecting the latency having the largest number of peaks located thereabout as the first fixed latency.

85. The apparatus for determining proximity of a nerve to a second conductive element of claim 82, further comprising:

(a) means for determining the peaks in the responses of the nerve to the first applied electrical signal for the plurality of predetermined current levels;

(b) means for determining the ratio of the peak level to corresponding current level for each peak;

(c) means for determining the sum of the ratio of peak level to current level for peaks located about each latency having a peak located thereabout; and (d) means for selecting the latency having the largest sum of ratios as the first fixed latency.

86. The apparatus for determining proximity of a nerve to a second conductive element of claim 85, wherein each response is an EMG.

87. The apparatus for determining proximity of a nerve to a second conductive element of claim 85, wherein each response is an EMG measured at a muscle physiologically coupled to the nerve.

88. The apparatus for determining proximity of a nerve to a second conductive element of claim 87, wherein the second fixed latency is equal to the first fixed latency.

89. A method of determining proximity of a nerve to a conductive element comprising the steps of:

(a) applying a first electrical signal having a plurality of predetermined current levels to the conductive element while the conductive element is disposed at a first location;

(b) measuring the responses of the nerve to the first applied electrical signal for the plurality of predetermined current levels;

(c) applying a second electrical signal having the plurality of predetermined current levels to the conductive element while the conductive element is disposed at a second location;

(d) measuring the responses of the nerve to the second applied electrical signal for the plurality of predetermined current levels; and (e) determining the nerve proximity to the conductive element based on the responses of the nerve to the first applied electrical signal for the plurality of predetermined current levels and the responses of the nerve to the second applied electrical signal for the plurality of predetermined current levels.

90. The method of claim 89, wherein step e) includes determining the nerve proximity to the conductive element based on the responses of the nerve to the first applied electrical signal for the plurality of predetermined current levels relative to the responses of the nerve to the second applied electrical signal for the plurality of predetermined current levels.

91. The method of claim 89, wherein step e) includes the sub-steps of: (i) mapping the responses of the nerve to the first applied electrical signal for the plurality of predetermined current levels; (ii) mapping the responses of the nerve to the second applied electrical signal for the plurality of predetermined current levels; and (iii) interpreting the mapped responses of the first and second applied electrical signals to determine nerve proximity to the conductive element.

92. The method of claim 91, wherein the step of interpreting the mapped responses involves comparing the slope of the mapped response for the first applied electrical signal to the slope of the mapped response for the second applied electrical signal.

93. The method of claim 91, wherein the step of interpreting the mapped responses involves comparing a current level of the mapped response for the first applied electrical signal to a current level of the mapped response for the second applied electrical signal.

94. The method of claim 89, wherein step e) of determining nerve proximity to the conductive element is performed intraoperatively to guide a real time procedure.

95. The method of claim 89, wherein the conductive element is coupled to a medical device.

96. The method of claim 95, wherein the medical device comprises at least one of a cannula, a catheter, and a needle.

97. The method of claim 89, wherein each response is an EMG.

98. The method of claim 89, wherein each response is an EMG measured at a muscle physiologically coupled to the nerve.

99. An article of manufacture for use in determining proximity of a nerve to a conductive element, the article of manufacture comprising computer readable storage media including program logic embedded therein that causes control circuitry to perform the steps of:

(a) applying a first electrical signal having a plurality of predetermined current levels to the conductive element while the conductive element is disposed at a first location;

(b) measuring the responses of the nerve to the first applied electrical signal for the plurality of predetermined current levels;

(c) applying a second electrical signal having the plurality of predetermined current levels to the conductive element while the conductive element is disposed at a second location;

(d) measuring the responses of the nerve to the second applied electrical signal for the plurality of predetermined current levels; and (e) determining the nerve proximity to the conductive element based on the responses of the nerve to the first applied electrical signal for the plurality of predetermined current levels and the responses of the nerve to the second applied electrical signal for the plurality of predetermined current levels.

100. The article of manufacture of claim 99, wherein step e) includes determining the nerve proximity to the conductive element based on the responses of the nerve to the first applied electrical signal for the plurality of predetermined current levels relative to the responses of the nerve to the second applied electrical signal for the plurality of predetermined current levels.

101. The article of manufacture of claim 99, wherein step e) includes the sub-steps of: (i) mapping the responses of the nerve to the first applied electrical signal for the plurality of predetermined current levels; (ii) mapping the responses of the nerve to the second applied electrical signal for the plurality of predetermined current levels; and (iii) interpreting the mapped responses of the first and second applied electrical signals to determine nerve proximity to the conductive element.

102. The article of manufacture of claim 101, wherein the step of interpreting the mapped responses involves comparing the slope of the mapped response for the first applied electrical signal to the slope of the mapped response for the second applied electrical signal.

103. The article of manufacture of claim 101, wherein the step of interpreting the mapped responses involves comparing a current level of the mapped response for the first applied electrical signal to a current level of the mapped response for the second applied electrical signal.

104. The article of manufacture of claim 99, wherein step e) of determining nerve proximity to the conductive element is performed intraoperatively to guide a real time procedure.

105. The article of manufacture of claim 99, wherein the conductive element is coupled to a medical device.

106. The article of manufacture of claim 105, wherein the medical device comprises at least one of a cannula, a catheter, and a needle.

107. The article of manufacture of claim 99, wherein each response is an EMG.

108. The article of manufacture of claim 99, wherein each response is an EMG measured at a muscle physiologically coupled to the nerve.

109. An apparatus for determining proximity of a nerve to a conductive element, the apparatus comprising:

(a) means for applying a first electrical signal having a plurality of predetermined current levels to the conductive element while the conductive element is disposed at a first location;

(b) means for measuring the responses of the nerve to the first applied electrical signal for the plurality of predetermined current levels;

(c) means for applying a second electrical signal having the plurality of predetermined current levels to the conductive element while the conductive element is disposed at a second location;

(d) means for measuring the responses of the nerve to the second applied electrical signal for the plurality of predetermined current levels; and (e) means for determining the nerve proximity to the conductive element based on the responses of the nerve to the first applied electrical signal for the plurality of predetermined current levels and the responses of the nerve to the second applied electrical signal for the plurality of predetermined current levels.

110. The apparatus of claim 109, wherein the means for determining the nerve proximity to the conductive element includes means for determining the nerve proximity to the conductive element based on the responses of the nerve to the first applied electrical signal for the plurality of predetermined current levels relative to the responses of the nerve to the second applied electrical signal for the plurality of predetermined current levels.

111. The apparatus of claim 109, wherein the means for determining the nerve proximity to the conductive element includes: (i) means for mapping the responses of the nerve to the first applied electrical signal for the plurality of predetermined current levels; (ii) means for mapping the responses of the nerve to the second applied electrical signal for the plurality of predetermined current levels; and (iii) means for interpreting the mapped responses of the first and second applied electrical signals to determine nerve proximity to the conductive element.

112. The apparatus of claim 111, wherein the means for interpreting the mapped responses includes means for comparing the slope of the mapped response for the first applied electrical signal to the slope of the mapped response for the second applied electrical signal.

113. The apparatus of claim 111, wherein the means for interpreting the mapped responses includes means for comparing a current level of the mapped response for the first applied electrical signal to a current level of the mapped response for the second applied electrical signal.

114. The apparatus of claim 109, wherein the determination of nerve proximity to the conductive element is performed intraoperatively to guide a real time procedure.

115. The apparatus of claim 109, wherein the conductive element is coupled to a medical device.

116. The apparatus of claim 115, wherein the medical device comprises at least one of a cannula, a catheter, and a needle.

117. The apparatus of claim 109, wherein each response is an EMG.

118. The apparatus of claim 109, wherein each response is an EMG measured at a muscle physiologically coupled to the nerve.

* * * * *